United States Patent
Narula et al.

(10) Patent No.: US 7,361,630 B2
(45) Date of Patent: Apr. 22, 2008

(54) ALKYL SUBSTITUTED OCTENNITRILE DERIVATIVES

(75) Inventors: Anubhav P. S. Narula, Hazlet, NJ (US); Adam Jan Janczuk, Parlin, NJ (US)

(73) Assignee: International Flavors & Fragranies Inc., New York, NY (US)

( * ) Notice: Subject to any disclaimer, the term of this patent is extended or adjusted under 35 U.S.C. 154(b) by 321 days.

(21) Appl. No.: 11/220,931

(22) Filed: Sep. 7, 2005

(65) Prior Publication Data

US 2007/0055082 A1    Mar. 8, 2007

(51) Int. Cl.
*C11D 3/50*    (2006.01)

(52) U.S. Cl. .......................... 510/101; 512/6; 558/435

(58) Field of Classification Search ................ 510/101; 512/6; 558/435
See application file for complete search history.

(56) References Cited

FOREIGN PATENT DOCUMENTS

| EP | 0 025 939 B1 | 9/1979 |
| EP | 0025939 | 4/1981 |
| EP | 0135719 | 4/1985 |
| GB | 1018836 | 2/1966 |
| WO | WO 00/24705 | 5/2000 |

OTHER PUBLICATIONS

Yamamoto, T. et al. "Olfactory study on optically active citronellyl derivatives" Flavour and Fragrance J. (2004). 19(2): 121-133.
Phadke, A. S. et al. "Synthesis Of Norphytene And Its Isomer 2,6,10,14-Tetramethyl-Pentadec-2-ene" Indian J. Chem. Section B (1986) 25(12):1249-1250.

*Primary Examiner*—John R. Hardee
(74) *Attorney, Agent, or Firm*—Elizabeth M. Quirk; Joseph F. Leightner; XuFan Tseng

(57) ABSTRACT

The present invention is directed to novel cyclopropanecarbonitrile compounds of the general formula

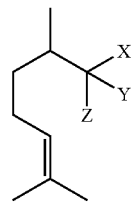

wherein X is a hydrogen, or a straight, branched, or cyclic hydrocarbon moiety consisting of less then 30 carbon atoms and containing single and/or double bonds; Z is a hydrogen or a straight, branched, or cyclic hydrocarbon moiety consisting of 1 to 30 carbon atoms and containing single and/or double bonds and Y is a nitrile.

13 Claims, No Drawings

ALKYL SUBSTITUTED OCTENNITRILE DERIVATIVES

FIELD OF THE INVENTION

The present invention relates to new chemical entities and the incorporation and use of the new chemical entities as fragrance materials.

BACKGROUND OF THE INVENTION

There is an ongoing need in the fragrance industry to provide new chemicals to give perfumers and other persons ability to create new fragrances for perfumes, colognes and personal care products. Those with skill in the art appreciate how differences in the chemical structure of the molecule can result in significant differences in the odor, notes and characteristics of a molecule. These variations and the ongoing need to discover and use the new chemicals in the development of new fragrances allows perfumers to apply the new compounds in creating new fragrances.

SUMMARY OF THE INVENTION

The present invention provides novel chemicals, and the use of the chemicals to enhance the fragrance of perfumes, toilet waters, colognes, personal products and the like. In addition, the present invention is directed to the use of the novel chemicals to enhance fragrance in perfumes, toilet waters, colognes, personal products and the like.

More specifically, the present invention is directed to the novel alkyl substituted octennitrile compounds, represented by the general structure of Formula I set forth below:

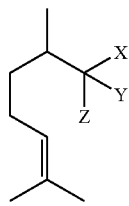

Formula I wherein X is a hydrogen, or a straight, branched, or cyclic hydrocarbon moiety consisting of less then 30, preferably less then 15, most preferably less then 7 carbon atoms and containing single and/or double bonds; Z is a hydrogen or a straight, branched, or cyclic hydrocarbon moiety consisting of less then 30, preferably less then 15, most preferably less then 7 carbon atoms and containing single and/or double bonds and Y is a nitrile.

Another embodiment of the invention is a method for enhancing a perfume by incorporating an olfactory acceptable amount of the compounds provided above.

These and other embodiments of the present invention will be apparent by reading the following specification.

DETAILED DESCRIPTION OF THE INVENTION

In Formula I above, X and Z represent a hydrogen or a straight, branched, or cyclic hydrocarbon moiety consisting of less then 30, preferably less then 15, most preferably less then 7 carbon atoms and containing single and/or double bonds. Suitable straight hydrocarbon moieties include ethyl, propyl, butyl, pentyl, hexyl, and the like. Suitable branched hydrocarbon moieties include isopropyl, sec-butyl, tert-butyl, 2-ethyl-propyl, and the like. Suitable cyclic hydrocarbon moieties include cyclopropane, cyclobutane, cyclopentane, cyclopentene, 1,4-cyclopentene, cyclohexane, cyclohexene and the like. Suitable hydrocarbon moieties containing double bonds include ethene, propene, 1-butene, 2-butene, penta-1-3-deine, hepta-1,3,5-triene and the like.

In the preferred embodiment of the invention, the novel compounds of the present invention are represented by the following structures:

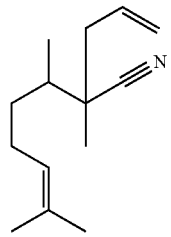

Formula II

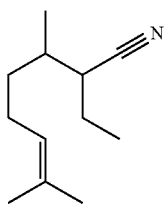

Formula III

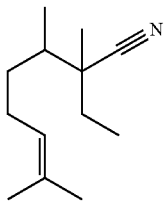

Formula IV

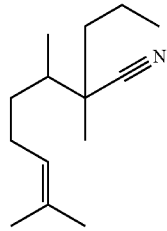

Formula V

-continued

Formula VI
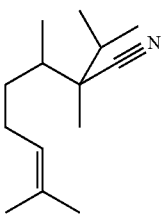

Formula VII
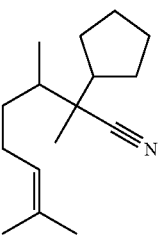

Formula VIII
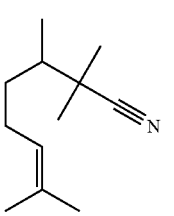

Formula IX
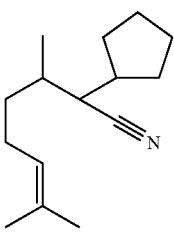

Formula X
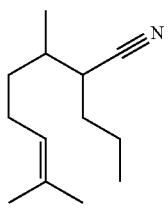

Formula XI
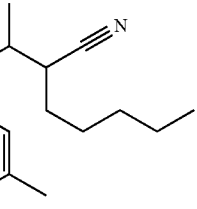

Formula XII
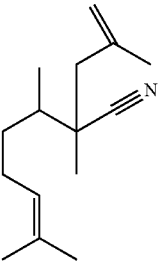

Those with the skill in the art will appreciate that the compound of Formula II is 2-Allyl-2,3,7-trimethyl-oct-6-enenitrile; the compound of Formula III is 2-Ethyl-3,7-dimethyl-oct-6-enenitrile; the compound of Formula IV is 2-Ethyl-2,3,7-trimethyl-oct-6-enenitrile; the compound of Formula V is 2,3,7-Trimethyl-2-propyl-oct-6-enenitrile; the compound of Formula VI is 2-Isopropyl-2,3,7-trimethyl-oct-6-enenitrile; the compound of Formula VII is 2-Cyclopentyl-2,3,7-trimethyl-oct-6-enenitrile; the compound of Formula VIII is 2,2,3,7-Tetramethyl-oct-6-enenitrile; the compound of Formula IX is 2-Cyclopentyl-3,7-dimethyl-oct-6-enenitrile; the compound of Formula X is 3,7-dimethyl-2-propyl-oct-6-enenitrile; the compound of Formula XI is 3,7-dimethyl-2-pentyl-oct-6-enenitrile and the compound of Formula XII is 2,3,7-Trimethyl-2-(2-methyl-allyl)-oct-6-enenitrile.

In the table below, the compounds of the present invention are listed with their respective scent.

TABLE 1

| COMPOUND | SCENT |
|---|---|
| 6-octenenitrile, 3,7-dimethyl-2-pentyl | Green, citrus fresh |
| 6-octenenitrile, 3,7-dimethyl-2-(2-propenyl) | Fishy |
| 6-octenenitrile, 3,7-dimethyl-2-(1-methylethyl) | Weak |
| 6-octenenitrile, 3,7-dimethyl-2-(2-methyl-2-propenyl) | Weak, citrus |
| 6-octenenitrile, 3,7-dimethyl-2-propyl | Mango, citrus |
| Cyclopentane acetonitrile, alpha-(1,5-dimethyl-4-hexenyl) | Amine |
| 6-octenenitrile, 2,3,7-trimethyl-2-pentyl | White mushroom, white chocolate |
| 6-octenenitrile, 2,2,3,7-tetramethyl | Lemon, powerful |
| Cyclopentane acetonitrile, alpha-(1,5-dimethyl-4-hexenyl)-alpha-methyl | Weak |
| 6-octenenitrile, 2,3,7-trimethyl-2-(2-methyl-2-propenyl) | Floral, rosey |
| 6-octenenitrile, 2,3,7-trimethyl-2-(1-methylethyl) | Weak |
| 6 (or 7)-octenenitrile, 2,3,7-trimethyl (isomer mix) | Citrus, geraniol |
| 6-octenenitrile, 2,3,7-trimethyl-2-propyl | Herbacious, spicy |
| 6-octenenitrile, 2-ethyl-2,3,7-trimethyl | Citrus, fresh |
| 6-octnenitrile, 2-ethyl-3,7-dimethyl | Marine-like |
| 6-octenenitrile, 2,3,7-trimethyl-2-(2-propyl) | Weak |
| 6-octenamide, 3,7-dimethyl | Powerful, citrus |
| 6-octen-1-ol, 2,3,7-trimethyl | Rosey, geraniol, natural |

As described in the examples below, the compounds of the present invention may be prepared from compound of Formula XIII by following the reaction sequence shown below:

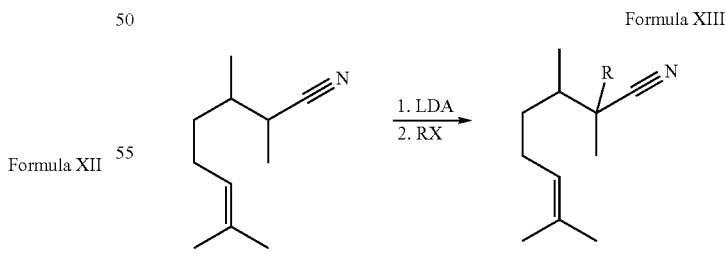

Formula XIII wherein LDA is Lithium Diisopropyl Amide, R is any alkyl group and X is a halogen, such as Cl, Br, or I.

As indicated in the examples below, the compound of Formula XIII is 2,3,7-Tetramethyl-oct-6-enenitrile. The preparation of this compound is disclosed in EP 025 939.

Those with skill in the art will recognize that the compounds of the present invention have a number of chiral centers, thereby providing several isomers of the claimed compounds. It is intended herein that the compounds described herein include isomeric mixtures of such compounds, as well as those isomers that may be separated using techniques known to those having skill in the art. Suitable techniques include chromatography such as HPLC, and particularly gel chromatography and solid phase microextraction ("SPME").

The use of the compounds of the present invention is widely applicable in current perfumery products, including the preparation of perfumes and colognes, the perfuming of personal care products such as soaps, shower gels, and hair care products as well as air fresheners and cosmetic preparations. The present invention can also be used to perfume cleaning agents, such as, but not limited to detergents, dishwashing materials, scrubbing compositions, window cleaners and the like.

In these preparations, the compounds of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

Olfactory effective amount is understood to mean the amount of compound in perfume compositions the individual component will contribute to its particular olfactory characteristics, but the olfactory effect of the perfume composition will be the sum of the effects of each of the perfumes or fragrance ingredients. Thus the compounds of the invention can be used to alter the aroma characteristics of the perfume composition, or by modifying the olfactory reaction contributed by another ingredient in the composition. The amount will vary depending on many factors including other ingredients, their relative amounts and the effect that is desired.

The level of compound of the invention employed in the perfumed article varies from about 0.005 to about 10 weight percent, preferably from about 0.5 to about 8 and most preferably from about 1 to about 7 weight percent. In addition to the compounds other agents can be used in conjunction with the fragrance. Well known materials such as surfactants, emulsifiers, polymers to encapsulate the fragrance can also be employed without departing from the scope of the present invention.

Another method of reporting the level of the compounds of the invention in the perfumed composition, i.e., the compounds as a weight percentage of the materials added to impart the desired fragrance. The compounds of the invention can range widely from 0.005 to about 70 weight percent of the perfumed composition, preferably from about 0.1 to about 50 and most preferably from about 0.2 to about 25 weight percent. Those with skill in the art will be able to employ the desired level of the compounds of the invention to provide the desired fragrance and intensity.

The following are provided as specific embodiments of the present invention. Other modifications of this invention will be readily apparent to those skilled in the art. Such modifications are understood to be within the scope of this invention. As used herein all percentages are weight percent unless otherwise noted, ppm is understood to stand for parts per million and g is understood to be grams.

EXAMPLE I

Preparation of 2,2,3,7-Tetramethyl-oct-6-enenitrile

To a two liter round bottom reaction vessel fitted with a stirrer flushed with $N_2$, 128.5 g of Lithium Diisopropyl Amide (LDA) was charged to the vessel which was cooled to 0° C. 165.2 g of 2,3,7-Tetramethyl-oct-6-enenitrile was charged over a period of 45 minutes. Then 177 grams of methyl iodide was charged over an hour. The contents were allowed to react for about 6 hours at 19° C.

The reaction was quenched with 1.5 m HCl, washed with water, washed with $NaHCO_3$; and then washed with brine.

The contents were purified with fractional distillation to yield 203 grams of product for a yield of about 57%.

The NMR of 2,2,3,7-Tetramethyl-oct-6-enenitrile is as follows: 1.0 ppm (s, 3H); 1.2 ppm (s, 1H); 1.3 ppm (s, 6H); 1.5 ppm (s, 1H); 1.6 ppm (s, 3H); 1.7 ppm (s, 1H); 1.8 ppm (s, 4H); 2.0 ppm (m, 1H); 2.1 ppm (s, 1H); 5.1 ppm (s, 1H).

EXAMPLE II

Preparation of 2.3,7-Trimethyl-2-propyl-oct-6-enenitrile

Using similar equipment described in Example I, 128.5 grams of LDA was charged to the vessel and cooled to 0° C. 165 grams of 2,3,7-Trimethyl-oct-6-enenitrile was charged over a period of 30 minutes, then iodo propane (212.5 grams) was charged and the contents were allowed to age at room temperature for about 8.5 hours.

The product was quenched twice with two washes of HCl, a water wash, a $NaHCO_3$ wash and a brine wash.

The product was purified by fractional distillation yielding about 100 grams, for a yield of about 48.6%

The NMR of 2,3,7-Trimethyl-2-propyloct-6-enenitrile is as follows: 1.0 ppm (s, 3H); 1.1 ppm (s, 1H); 1.2 ppm (m, 1H); 1.3 ppm (s, 4H); 1.5 ppm (m, 2H); 1.6 ppm (s, 1H) 1.6 ppm (s, 3H); 1.7 ppm (s, 2H); 2.0 ppm (m, 1H); 2.1 ppm (s, 1H); 5.1 ppm (s, 1H).

EXAMPLE III

Preparation of 2-Allyl-2,3,7-trimethyl-oct-6-enenitrile

Using the equipment of Example I, 479 grams of LDA (2.0 m THF/Heptane) was charged to the vessel and cooled to 0° C. 165 grams of 2,3,7-Trimethyl-oct-6-enenitrile was charged over about 30 minutes, sodium iodide (3.75 grams) was added, then allyl chloride (92 grams) was added dropwise while maintaining the temperature below about 10° C. The allyl chloride was added over a period of 40 minutes and the contents were allowed to age for several hours.

The product was quenched with HCl, two water washes, two NaHCO₃ and a brine wash. The product (1576 grams) was recovered by fractional distillation for a yield of about 77%.

The NMR of 2-Allyl-2,3,7-trimethyl-oct-6-enenitrile is as follows: 1.0.ppm (s; 1H); 1.1 ppm (s, 1H); 1.2 ppm (m, 1H); 1.3 ppm (s, 3H); 1.6 ppm (s, 4H); 1.7 ppm (s, 4H) 2.0 ppm (s, 1H); 2.1 ppm (s, 1H); 2.2 ppm (m, 1H); 2.4 ppm (m, 1H); 5.1 ppm (d, 1H); 5.2 ppm (s, 1H); 5.3 ppm (d, 2H); 5.9 ppm (m, 1H).

EXAMPLE IV

Preparation of 2,3,7-Trimethyl-2-(2-methyl-allyl)-oct-6enenitrile

Using the equipment of Example I, 479 grams of LDA (2.0 m THF/Heptane) was charged to the vessel and cooled to 0° C. 165 grams of 2,3,7-Trimethyl-oct-6-enenitrile was slowly fed to the reactor over 45 minutes. 3-chloro-2-methyl propane (113 grams) and then sodium iodine was added (3.75 grams).

The feeds completed and the contents were allowed to cool to room temperature and age for about 8 hours.

The contents were quenched with 1.5 m HCl, washed twice with water, once with NaHCO₃ and finally with brine.

Fractional distillation provided 131 grams of product for a yield of 59.7%.

The NMR of 2,3,7-Trimethyl-2-(2-methyl-allyl)-oct-6-enenitrile is as follows: 1.0 ppm (s, 1H); 1.1 ppm (s, 2H); 1.2 ppm (m, 1H); 1.3 ppm (s, 3H); 1.6 ppm (s, 5H); 1.7 ppm (s, 4H) 1.9 ppm (s, 3H); 2.0 ppm (m, 1H); 2.2 ppm (d, 2H); 2.4 ppm (m, 1H); 4.8 ppm (s, 1H); 5.0 ppm (s, 1H); 5.1 ppm (d, 2H).

EXAMPLE V

Preparation of 2-Isopropyl-2,3,7-trimethyl-oct-6-enenitrile

To the equipment described in Example I 479 grams of LDA (2.0 m THF/Heptane) was charged to the vessel and cooled to 0° C. 165 grams of 2,3,7-Trimethyl-oct-6-enenitrile was charged over 45 minutes. 2-iodo propane (212.5 grams) was fed over about 2 hours at which point the contents were allowed to reach room temperature. The contents were aged for 8 hours.

The product was then washed with 1.5 m HCl, once with NaHCO₃ and then brine. The product was then isolated using fractional distillation providing about 135 grams for about 65% yield.

The NMR of 2-Isopropyl-2,3,7-trimethyl-oct-6-enenitrile is as follows: 0.9 ppm (s, 2H); 1.0 ppm (s,3H); 1.1 ppm (s, 1H); 1.1 ppm (m, 1H); 1.2 ppm (s, 3H); 1.3 ppm (m, 1H); 1.5 ppm (m, 1H) 1.6 ppm (s, 3H); 1.7 ppm (s, 3H); 1.8 ppm (m, 1H); 2.0 ppm (m, 2H); 2.1 ppm (s, 1H); 5.1 ppm (s, 1H).

EXAMPLE VI

Preparation of 2-Cyclopentyl-2,3,7-trimethyl-oct-6enenitrile

Using similar equipment as described in Example I, 479 grams of LDA (2.0 m THF/Heptane) was charged to the vessel and cooled to 0° C. 165 grams of 2,3,7-Trimethyl-oct-6-enenitrile was charged over about 45 minutes. Then sodium iodide (3.75 grams) was added followed by cyclopentyl bromide (186 grams, 98%) was charged and the contents allowed to reach room temperature. The contents were allowed to age for 8 hours.

The product was quenched with 1.5 m HCl, then with NaHCO₃ and finally with brine. Fractional distillation provided about 138 grams for a yield of 59%.

The NMR of 2-Cyclopentyl-2,3,7-trimethyl-oct-6-enenitrile is as follows: 0.9 ppm (s, 1H); 1.0 ppm (m, 1H); 1.1 ppm (s, 2H); 1.2 ppm (s, 3H); 1.3 ppm (m, 1H); 1.5 ppm (m, 3H); 1.6 ppm (s, 2H) 1.6 ppm (s, 3H); 1.7 ppm (s, 4H); 1.8 ppm (m, 5H); 1.9-2.1 ppm (m, 2H); 2.2 ppm (s, 1H); 2.6 ppm (s, 1H); 5.1 ppm (d, 1H); 7.1-7.3 ppm (m, 1H).

EXAMPLE VII

Preparation of 2-Cyclopentyl-3,7-dimethyl-oct-6-enenitrile

Using the equipment described above, 479 grams of LDA (2.0 m THF/Heptane) was charged to the vessel and cooled to 0° C. Sodium iodide (3.75 grams) was charged followed by the slow addition of citronalva (151 grams) over about 45 minutes. Cyclopentyl bromide (182 grams, 98%) was added over 30 minutes and the contents allowed to warm to room temperature. The contents were aged for about 6 hours.

The product was worked up with 1.5 m MCl, washedwith aqueous NaHCO₃ and finally with two washes of brine.

Fractional distillation yielded 131.8 grams of product for a yield of about 60%.

The NMR of 2-Cyclopentyl-3,7-dimethyl-oct-6-enenitrile is as follows: 1.0 ppm (s, 3H); 1.1-1.3 ppm (m, 2H); 1.4-1.5 ppm (m, 2H); 1.6 ppm (s, 2H) 1.6 ppm (s, 4H); 1.7 ppm (s, 6H); 1.8 ppm (s, 1H); 1.9-2.0 ppm (m, 3H); 2.1 ppm (m, 1H); 2.4 ppm (m, 1H); 5.1 ppm (d, 1H); 7.1-7.3 ppm (m, 1H).

EXAMPLE VIII

Preparation of 2-Ethyl-3,7-dimethyl-oct-6-enenitrile

Using equipment similar to the previous exmaples, LDA (2.0 m, 234.9 grams) was charged to the vessel. Citronalva (302 grams) was then added while maintaining the temperature below about 30° C. over about 2.5 hours. The contents were then cooled to about −10° C. and then ethyl iodide (319.7 grams) was added over about 45 minutes. The contents were allowed to warm to room temperature and age for about 3 hours.

The product was worked up using 1.5 m HCl, two washes of aqueous NaHCO₃ and finally twice with brine.

Fractional distillation provided 196.2 grams of product for a yield of 54.7%.

The NMR of 2-Ethyl-3,7-dimethyl-oct-6-enenitrile is as follows: 1.0-1.1 ppm (d, 6H); 1.2-1.3 ppm (m, 1H); 1.4 ppm (m, 1H); 1.5 ppm (s, 4H); 1.6 ppm (s, 3H); 1.8 ppm (d, 5H); 1.9-2.2 ppm (m, 2H); 2.3 ppm (m, 1H); 2.5 ppm (m, 1H); 4.7 ppm (d, 1H); 5.1 ppm (s, 1H).

EXAMPLE IX

Preparation of 2-Ethyl-2,3,7-trimethyl-oct-6-enenitrile

Using similar equipment as described previously, 479 grams of LDA (2.0 m THF/Heptane) was charged to the vessel and cooled to 0° C. 165 grams of 2,3,7-Trimethyl-oct-6-enenitrile was added over about 40 minutes. Ethyl iodide (187 grams) was then added while maintaining temperature below about 10° C. The contents were allowed to warm to room temperature and age for about 4 hours.

The product was worked up by quenching with 1.5 m HCl, an aqueous $NaHCO_3$ wash and a brine wash.

Fractional distillation provided 125.7 grams of product for a yield of about 65%.

The NMR of 2-Ethyl-2,3,7-trimethyl-oct-6-enenitrile is as follows: 1.0 ppm (s, 1H); 1.1 ppm (s, 6H); 1.3 ppm (s, 4H); 1.5 ppm (m, 2H); 1.6 ppm (s, 4H); 1.8 ppm (s, 5H); 2.0 ppm (m, 1H); 2.1 ppm (s, 1H); 5.1 ppm (s, 1H).

What is claimed is:

1. A compound of formula

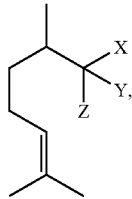

wherein X is a straight, branched, or cyclic hydrocarbon moiety consisting of less than 30 carbon atoms and containing single and/or double bonds; Z is a straight, branched, or cyclic hydrocarbon moiety consisting of less than 30 carbon atoms and containing single and/or double bonds and Y is a nitrile.

2. The compound of claim 1, wherein X is hydrocarbon moiety consisting of less than 15 carbon atoms.

3. The compound of claim 1, wherein X is hydrocarbon moiety consisting of less than 7 carbon atoms.

4. The compound of claim 1, wherein Z is hydrocarbon moiety consisting of less than 15 carbon atoms.

5. The compound of claim 1, wherein Z is hydrocarbon moiety consisting of less than 7 carbon atoms.

6. A method of improving, enhancing or modifying a fragrance formulation through the addition of an olfactory acceptable amount of the compound of claim 1.

7. The method of claim 6, wherein the fragrance formulation is incorporated into a product selected from the group consisting of a perfume, a cologne, a toilet water, a cosmetic product, a personal care product, a fabric care product, a cleaning product and an air freshener.

8. The method of claim 7, wherein the cleaning product is selected from the group consisting of a detergent, a dishwashing composition, a scrubbing compound and a window cleaner.

9. The method of claim 6, wherein the amount added into the fragrance formulation is from about 0.005 to about 10 weight percent.

10. The method of claim 6, wherein the amount added into the fragrance formulation is from about 0.5 to about 8 weight percent.

11. The method of claim 6, wherein the amount added into the fragrance formulation is from about 1 to about 7 weight percent.

12. A fragrance formulation containing an olfactory effective amount of the compound of claim 1.

13. A fragrance product containing the compound of claim 1.

* * * * *